United States Patent [19]

Ávár

[11] Patent Number: 4,921,893

[45] Date of Patent: * May 1, 1990

[54] STABILIZING POLYMERS

[75] Inventor: Lajos Ávár, Biel-Benken, Switzerland

[73] Assignee: Sandoz Ltd., Basel, Switzerland

[*] Notice: The portion of the term of this patent subsequent to Dec. 29, 2004 has been disclaimed.

[21] Appl. No.: 128,363

[22] Filed: Dec. 3, 1987

Related U.S. Application Data

[60] Division of Ser. No. 712,345, Mar. 15, 1985, Pat. No. 4,716,187, which is a continuation-in-part of Ser. No. 590,506, Mar. 16, 1984, abandoned.

[30] Foreign Application Priority Data

Mar. 21, 1983 [DE] Fed. Rep. of Germany ....... 3310100

[51] Int. Cl.$^5$ .......................... C08K 5/34; C08K 5/35; C07D 211/58; C07D 401/12

[52] U.S. Cl. ..................... 524/99; 524/102; 524/103; 546/16; 546/18; 546/188; 546/189; 546/190; 546/191; 546/216; 546/223; 252/402; 252/403; 106/285; 106/287.2

[58] Field of Search ............... 252/402, 403; 524/99, 524/102, 103; 546/16, 18, 216, 188, 189, 190, 191, 216, 223; 106/285, 287.2

[56] References Cited

U.S. PATENT DOCUMENTS

| | | | |
|---|---|---|---|
| 3,684,765 | 8/1972 | Matsui et al. | 524/99 |
| 3,904,581 | 9/1975 | Murayama et al. | 524/99 |
| 3,907,803 | 9/1975 | Ramey et al. | 524/99 |
| 4,348,524 | 9/1982 | Karrer et al. | 524/99 |
| 4,500,662 | 2/1985 | Lai | 524/99 |
| 4,716,187 | 12/1987 | Avar | 524/99 |
| 4,727,100 | 2/1988 | Vasta | 524/102 |
| 4,731,393 | 3/1988 | Karrer et al. | 524/102 |

FOREIGN PATENT DOCUMENTS

| | | | |
|---|---|---|---|
| 0034829 | 9/1981 | European Pat. Off. | |
| 58-77862 | 5/1983 | Japan | |
| 0670588 | 6/1979 | U.S.S.R. | 524/102 |

OTHER PUBLICATIONS

J. Med. Chem. 1982, 25, 1106–1110.

Primary Examiner—John Kight
Assistant Examiner—Kriellion Morgan
Attorney, Agent, or Firm—Gerald D. Sharkin; Richard E. Vila; Thomas C. Doyle

[57] ABSTRACT

$$\left[ R-N \underset{R_2\ R_2}{\overset{R_1\ R_1}{\diagup\!\!\!\diagdown}} N-CH_2CH_2-\overset{O}{\underset{\|}{C}}-X \right]_m R_4 \quad (I)$$

in which

R is hydrogen, unsubstituted $C_{1-18}$alkyl, unsubstituted $C_{1-21}$alkyl carbonyl, unsubstituted $C_{2-19}$alkenyl carbonyl, phenyl carbonyl, phenyl $C_{1-4}$alkyl carbonyl, $C_{1-4}$alkyl phenyl carbonyl or oxygen;

both $R_1$'s are $CH_3$ or together form $-(CH_2)_5-$;

both $R_2$'s are $CH_3$ or together form $-(CH_2)_5-$;

$R_3$ has a significance of R, independently of R, except for oxygen;

X is —O—, —NH— or $$-\underset{|}{N}(C_{1-4}\text{alkyl});$$

m is an integer from 1 to 4 inclusive;

$R_4$ is a saturated or unsaturated aliphatic group unsubstituted or substituted by one or two groups selected from —OH and $C_{1-4}$alkoxy and which can be interrupted by an oxygen or sulphur atom; or an aromatic group unsubstituted or substituted by one or two groups selected from —OH, $C_{1-4}$alkyl and $C_{1-4}$alkoxy are useful as U.V. light stabilizers in polymeric organic compounds.

25 Claims, No Drawings

STABILIZING POLYMERS

This is a division of application Ser. No. 712,345, filed Mar. 15, 1985, now U.S. Pat. No. 4,716,187, which in turn is a continuation-in-part of Ser. No. 590,506, filed Mar. 16, 1984, now abandoned.

The invention relates to 4-amino-polyalkyl piperidine compounds for use as U.V. light stabilisers in polymeric organic materials and to the use of such compounds, as well as products obtained thereby.

The compounds involved in this invention are those of formula I:

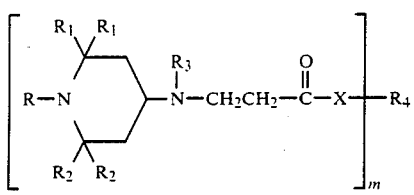

in which

R is hydrogen, unsubstituted $C_{1-18}$alkyl, unsubstituted $C_{1-21}$-alkyl carbonyl, unsubstituted $C_{2-19}$alkenyl carbonyl, phenyl carbonyl, pheny $C_{1-4}$alkyl carbonyl, $C_{1-4}$alkyl phenyl carbonyl or oxygen;

both $R_1$'s are $CH_3$ or together form $-(CH_2)_5-$;
both $R_2$'s are $CH_3$ or together form $-(CH_2)_5-$;
$R_3$ has a significance of R, independently of R, except for oxygen;
X is $-O-$, $-NH-$ or

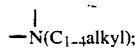

m is an integer from 1 to 4 inclusive;
$R_4$ is a saturated or unsaturated aliphatic group unsubstituted or substituted by one or two groups selected from $-OH$ and $C_{1-4}$alkoxy and which can be interrupted by an oxygen or sulphur atom; or an aromatic group unsubstituted or substituted by one or two groups selected from $-OH$, $C_{1-4}$alkyl and $C_{1-4}$alkoxy.

An embodiment of this invention is the provision of compounds of Formula Ia, ie compounds which are the same as compounds of Formula I, except that when m is 1, each of R and $R_3$ is hydrogen, each of $R_1$ and $R_2$ is methyl and X is oxygen, then $R_4$ is not ethyl.

In this specification where a significance appears more than once in a formula its significances are independent of one another unless indicated to the contrary.

All alkyl groups (containing more than 2 carbon atoms) and all alkenyl groups (containing more than 2 carbon atoms) are linear or branched.

Preferably, in R and $R_3$, $C_{1-21}$alkyl carbonyl is $C_{1-12}$alkyl carbonyl, more preferably $C_{1-4}$alkyl carbonyl.

Preferably, in R and $R_3$, $C_{2-19}$ alkenyl carbonyl is $C_{2-12}$alkenyl carbonyl, more preferably $C_{2-4}$alkenyl carbonyl.

Preferably R is R′ where R′ is hydrogen, $C_{1-4}$alkyl, $C_{1-12}$alkyl carbonyl or $C_{2-12}$alkenyl carbonyl. More preferably R is R″ where R″ is hydrogen $C_{1-4}$alkyl or $C_{1-4}$alkyl carbonyl. Most preferably R is R‴ where R‴ is hydrogen, methyl or

of which hydrogen and methyl are preferred; more preferred is hydrogen.

Preferaby $R_1$ and $R_2$ are $CH_3$.

Preferably $R_3$ is $R_3'$ where $R_3'$ is hydrogen, $C_{1-4}$alkyl, $C_{1-12}$alkyl carbonyl or $C_{2-12}$alkenyl carbonyl; more preferably $R_3$ is $R_3''$ where $R_3''$ where $R_3''$ is hydrogen, $C_{1-4}$alkyl or $C_{1-4}$alkyl carbonyl. Most preferably $R_3$ is $R_3'''$ where $R_3'''$ is hydrogen, methyl or

of which hydrogen and methyl are preferred, more preferred is hydrogen;

X is preferably $-O-$.

m is preferably m′ where m′ is 1, 2 or 4. More preferably m is m″ where m″ is 1 or 2.

$R_4$ is preferably $R_4'$ where $R_4'$ is $C_{1-18}$alkyl, $C_{1-8}$alkoxy-$C_{1-12}$Alkyl, $C_{1-6}$hydroxyalkyl, $C_{1-4}$alkyl cyclohexyl or linear or branched $C_{2-14}$alkylene uninterrupted or interrupted by $-O-$ or $-S-$.

Preferably when m=1 $R_4$ is $R_{4a}$ where $R_{4a}$ is $C_{1-18}$alkyl, $C_{1-8}$alkoxy-$C_{1-12}$alkyl, $C_{1-6}$hydroxy alkyl or $C_{1-4}$alkyl cyclohexyl.

Preferably when m=2 $R_4$ is $R_{4b}$ where $R_{4b}$ is

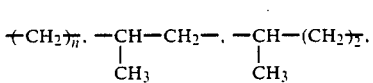

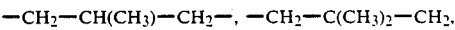

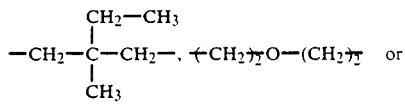

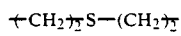

where n is 2 to 14. Preferably n is n′ where n′ is 4, 6, 8, 10 or 12. More preferably n is n″ where n″ is 4, 6 or 8. More preferably $R_{4b}$ is $R_{4b}'$ where $R_{4b}'$ is $-(CH_2)_{n''}-$ or $-(CH_2)_2-O-(CH_2)_2-$.

Preferably when m=3 $R_4$ is $R_{4c}$ where $R_{4c}$ is

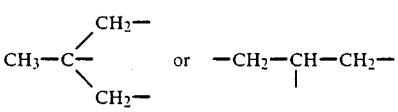

Preferably when m=4 $R_4$ is

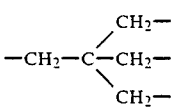

Preferred compounds of formula I are of formula I′

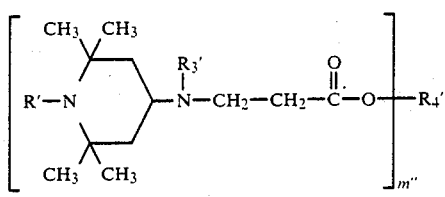

where the symbols R', $R_3'$, $R_4'$ and m' are as defined above.

More preferred compounds of formula I are of formula I''

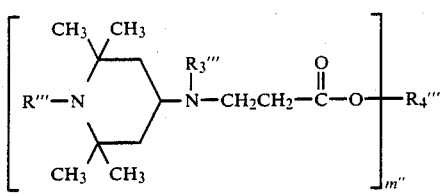

where R''', $R_3'''$ and m'' are as defined above and $R_4'''$ is $C_{1-18}$alkyl, $C_{2-6}$hydroxyalkyl, 4-tert.-butylcyclohexyl or $-(CH_2)_{\overline{n}'}$.

Compounds of formula I can be prepared by reacting a compound of formula II

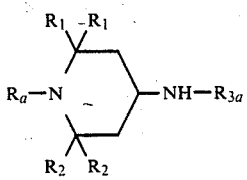

where $R_1$ and $R_2$ are above defined and $R_a$ and $R_{3a}$ independently
are hydrogen or $C_{1-18}$alkyl, with a compound of formula III

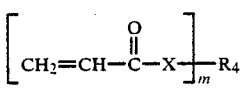

where X, $R_4$ and m are above defined, and, when R and/or $R_3$ are an acyl group (i.e. $C_{1-21}$alkyl carbonyl, $C_{2-19}$alkenyl carbonyl, phenyl carbonyl, phenyl $C_{1-4}$alkyl carbonyl or $C_{1-4}$alkyl phenyl carbonyl), acylating the resulting product where $R_a$ and/or $R_{3a}$ are hydrogen and when R is oxygen oxidising the product of reacting a compound of formula II where $R_a$ is hydrogen with a compound of formula III.

The acylation and oxidation reactions can be carried out according to known methods.

Compounds of formula II and III are known or can be made by known methods from known compounds.

Compounds of formula I where m is 2, 3 or 4 and where $R_4$ is other than methyl can be prepared by reacting a compound of formula IV

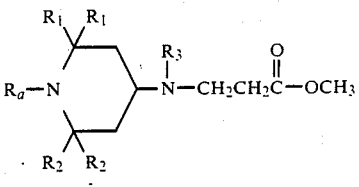

with a compound of formula V $$R_{4d}(OH)_m \quad (V)$$

where $R_{4d}$ has a significance of $R_4$ other than methyl.

Compounds of formula I where X=—NH— or —N($C_{1-4}$alkyl) can be prepared by amidating a compound of formula VI

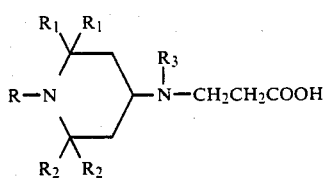

Both the ester exchange and the amidation reactions are known.

Compounds of formula I are useful as stabilizers to polymeric materials against degradation by light. The compounds have particularly good solubility and miscibility in solvent systems and in liquid polymers and prepolymers, which makes them useable in a wide range of polymeric materials.

The concentration of compound of formula I employed in the polymeric material is suitably 0.01 to 5% by weight, preferably 0.02 to 1% by weight. The compound may be added before, during or after the polymerization step, and may be added in solid form; in solution, preferably as a liquid concentrate containing from 20 to 80% by weight of compound of formula I; or as a solid masterbatch composition containing 20 to 80% by weight of compound of formula I and 80 to 20% by weight of a solid polymeric material which is identical with or compatible with the polymeric material to be stabilized.

Suitable polymeric materials include plastic materials for example polyethylene, polypropylene, ethylene/propylene copolymers, polyvinyl chloride, polyester; polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/formaldehyde resins and epoxy resins may also be used. Preferred plastic materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, films, tubes, containers, bottles, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compounds into thermosetting polymers, which cannot be melt blended.

The compounds of formula I may be used alone or in combination with other stabilizers, for example antioxidants. Examples include sterically hindered phenols, sulphur or phos- phorus-containing compounds or mixtures of these. Examples are benzofuran-2-ones; indolin-2-ones and sterically hindered phenols such as β-(4-hydroxy-3,5-ditert.-butylphenyl)-propionyl stearate, methane tetrakis-(methylene-3(3',5'-ditert.-butyl-4-hydroxyphenyl-)-propionate], 1,3,3-tris-(2-methyl-4-hydroxy-5-tert.-butylphenyl)-butane, 1,3,5-tris(4-tert.-butyl-3-hydroxy-2,6-dimethylbenzyl)-1,3,5-triazin-2,4,6 (1H, 3H, 5H)-trione, bis (4-tert.-butyl-3-hydroxy-2,6-dimethylbenzyl)dithiolterephthalate, tris(3,5-ditert.-butyl-4-hydroxybenzyl) isocyanurate, the triester of β-(4-hydroxy-3,5-ditert.-butylphenyl) propionic acid with 1,3,4-tris-(2-hydroxyethyl)-5-triazin-2,4,6 (1H, 3H, 5H)trione, bis [3,3-bis-(4'-hydroxy-3-tert.-butylphenyl)-butyric acid] glycol ester, 1,3,5-trimethyl-2,4,6 tris-(3,5-ditert.-butyl-4-hydroxy-benzyl) benzene, 2,2'-methylene-bis-(4-methyl-6-tert.-butylphenyl) terephthalate, 4,4-methylene-bis-(2,6-di-tert.-butylphenol), 4,4'-butylidene-bis-(tert.-butyl-metacresol), 2,2'-methylene-bis-(4-methyl-6-tert.-butyl-phenol.

Sulphur-containing antioxidative co-stabilizers which may be used include for example distearylthiodipropionate, dilaurylthiodipropionate, methane tetrakis (methylene-3-hexylthiopropionate), methane tetrakis (methylene-3-dodecylthiopropionate) and dioctadecyldisulphide. Phosphorus-containing co-stabilizers include for example trinonylphenyl phosphite, 4,9-distearyl-3,5,8,10-tetraoxadiphosphaspiroundecane, tris(2,4-ditert.-butylphenyl)phosphite and tetrakis (2,3-ditert.-butylphenyl)-4,4'-biphenylylene diphosphonite. Further additives such as aminoaryl compounds and U.V.-absorbers and light stabilizers e.g. 2-(2'-hydroxy-phenyl)-benzotriazole, 2-hydroxybenzophenone, 1,3-bis-(2'-hydroxybenzoyl)benzene, salicylates, cinnamates, benzoates and substituted benzoates, sterically hindered amines and oxalic acid diamides may be used. Other known types of additives, e.g. flame retardants and antistatic agents, may also be added.

The compounds of the invention can also be used in photopolymeric substrates containing photoinitiators for the photopolymerisation.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 80° C., in order to harden the finish in an acceptable time once it has been applied to the primer-coated metal surface. The hardening step may be accelerated by the use of an acid catalyst. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminium, in order to provide optical effects due to reflection. Such finishes are often two-coat finishes, in which a clear top coat finish is applied over a base coat finish containing a single pigment or metal flakes. The compounds of formula I can be in the top coat finish or the ground coat finish, preferably the former. Such two-coat metallic finishes have particular need of U.V.-stabilizers in the top coat, since the polymer in this coat is not protected by light-absorbing pigments, and it is subjected to almost double the normal amount of radiation because of reflection of light from the lower metallic layer.

The compounds of formula I are suitable for use as U.V.-stabilizers in a wide range of liquid finishes, for example those based on combinations of melamine-formaldehyde resins with oil-modified polyester resins, polyacrylate resins with added cross-linkers, or saturated polyesters; or on self-crosslinkers, or saturated polyesters; or on self-crosslinked polyacrylate or polyacrylate resin co-polymerised with styrene.

Further examples are two-component finishes based on an aliphatic or aromatic di-isocyanate and a hydroxy-group-containing polyacrylate, polyester or polyether resin. These polyurethane 2 component finishes are preferably hardened at 60° to 120° C. Thermoplastic polyacrylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins hardened with aliphatic di-isocyanates. In these cases it is preferred to use compounds of formula I in which R is alkyl or acyl.

The compounds of formula I are particularly useful in acid catalysed stoving finishes particularly in the top coat of two layer metallic finishes.

The compounds of formula I may be added to the finish at any stage in its manufacture, and may be added in solid form or in solution, preferably in the form of a liquid concentrate in a suitable solvent.

In practice the compounds of formula I are added to a finish as a solution in organic solvent (as a liquid finish) in which the binder material is between 35% (low solid finishes) and 70% by weight (high solid finishes). The binder material of the finish can be in aqueous emulsion or suspension form (as an aqueous finish) in which the binder material part makes up 20 to 30% by weight. However, the compounds of formula I can be added to known powder finishes.

The compounds of formula I are to be added to the liquid or powder finishes before stoving or hardening. Preferably the compounds of formula I are used in liquid finishes since it is easy to add exact dosages. It is particularly preferred to use a concentrate (preferably in a hydrocarbon solvent) containing at least 40% preferably 60 to 80% by weight of the total weight of the concentrate of a compound of formula I to introduce the compound of formula I to finishes for stoving.

The addition of from 0.01 to 5% by weight, preferably 0.2 to 2% by weight of one or more compounds of formula I gives a clear improvement in the light- and weather-stability of organic pigments in stoving finishes as well as reducing the tendency to hairline cracking and loss of gloss as the result of weathering. This is surprisingly also found for metallic finishes and excellent long-term stability of the clear top coat of two layer metallic finishes is obtained. In such finishes, the compound of formula I may be added to the metallic undercoat, the clear top coat or both, preferably only to the clear top coat. The metal surface to be finished may be under-coated with primer coatings as is customary in the art of coating metal surfaces.

The following Examples, in which all parts are by weight and all temperatures in degrees Centigrade illustrate the invention.

EXAMPLE 1

62.5 g of 4-amino-2,2,6,6-tetramethylpiperidine are dissolved in 500 ml of absolute alcohol and then reacted with 50 g of the ethyl ester of acrylic acid at 45° C. over 2 hours. The solution is then stirred for 2 hours at 80° C. and then for 20 hours at room temperature. The solvent is then distilled off in a rotary evaporator and the residue is distilled under vacuum. A compound of the formula 1a

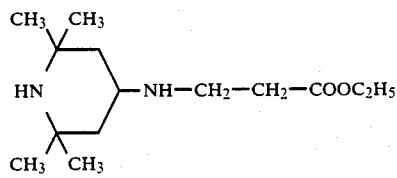
(1a)

results having a boiling point of 111° C. (0.8 mm Hg) as a colourless liquid. This compound can be used in a paint finish system.

EXAMPLE 2

15.6 g of 4-amino-2,2,6,6-tetramethylpiperidine are dissolved in 125 ml of methanol. Whilst stirring 18.0 g of butadiol-monoacrylate are added to the solution at 45° over 2 hours, after which the solution is stirred at 79° for 2 further hours and then left to stand overnight at room temperature. The solvent is then distilled off and the remaining reaction product is subjected to a high vacuum. A colourless thick oil results having a boiling point of 163°–164° C. (0.005 mm Hg) and is of the formula 2a

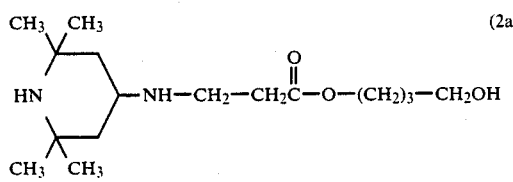
(2a)

EXAMPLES 3 to 18

In a manner analogous to that of Example 1 or 2 compounds of the formula

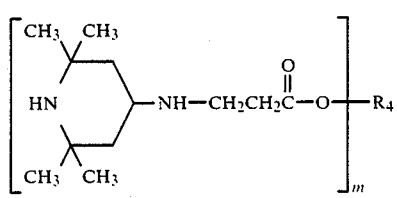

where the symbols m and $R_4$ are shown in Table 1 below, can be prepared from known starting products.

TABLE 1

| No. | m | $R_4$ |
|---|---|---|
| 3 | 1 | $C_2H_5$ |
| 4 | 1 | $C_4H_9$-n |
| 5 | 1 | $C_4H_9$-tert. |
| 6 | 1 | $C_8H_{17}$-n |
| 7 | 1 | $C_6H_{13}.C_2H_5$(ethylhexyl) |
| 8 | 1 | $C_{12}H_{25}$-n |
| 9 | 1 | $C_{12}H_{25}$(isomeric mixture) |
| 10 | 1 | $-(CH_2)_3-CH_2OH$ |
| 11 | 1 | $(CH_3)C-\langle H \rangle-$ |
| 12 | 2 | $-(CH_2)_3-$ |
| 13 | 2 | $-(CH_2)_4-$ |
| 14 | 2 | $-(CH_2)_6-$ |
| 15 | 2 | $-(CH_2)_2-O-(CH_2)_2-$ |
| 16 | 2 | $-(CH_2)_2-S-(CH_2)_2-$ |
| 17 | 3 | $CH_3-C(CH_2)_3-$ |
| 18 | 4 | $C(CH_2-)_4$ |

EXAMPLE 19

1.28 g of a compound of formula 1a (Example 1)

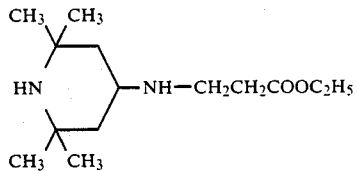
(1a)

and 2 g of dimethylformamide are mixed. The solution is reacted with 50 ml of acetic anhydride at room temperature whilst stirring and the temperature rises to 50°. The solution is then stirred for 20 hours at 90° C. The acetic anhydride is then distilled off using a water-jet vacuum and the residue is added to 100 ml of toluene, washed with water, the toluene solution is dried and then concentrated by removing the water as steam. The remaining oil is then crystallised from petrol (in the hexane fraction). A white product having a melting point of 70° to 72° of the formula (19a)

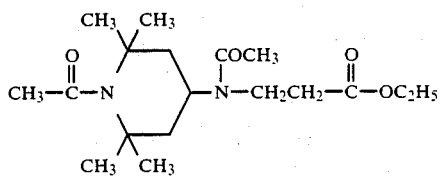
(19a)

is formed.

EXAMPLES 20 to 26

Compounds of the formula

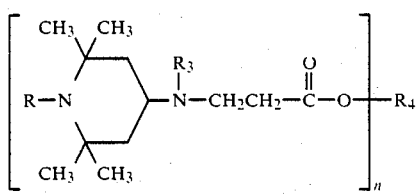

in which the symbols R, $R_3$, m and $R_4$ are defined in Table 2 below, can be prepared by a method analogous to Example 19 from known products.

TABLE 2

| No. | R | $R_3$ | m | $R_4$ |
|---|---|---|---|---|
| 20 | $CH_3\overset{O}{\underset{\|}{C}}-$ | $CH_3\overset{O}{\underset{\|}{C}}-$ | 1 | $C_8H_{17}$-(2-ethylhexyl) |
| 21 | $CH_3\overset{O}{\underset{\|}{C}}-$ | $C_8H_{17}-$ | 1 | $C_2H_5-$ |
| 22 | $CH_3\overset{O}{\underset{\|}{C}}-$ | $CH_3\overset{O}{\underset{\|}{C}}-$ | 1 | $C_{12}H_{25}-$ |
| 23 | $CH_3\overset{O}{\underset{\|}{C}}-$ | $CH_3\overset{O}{\underset{\|}{C}}-$ | 2 | $-(CH_2)_4-$ |
| 24 | $CH_3-$ | $CH_3-$ | 1 | $C_8H_{17}-$ |
| 25 | $CH_3-$ | $C_8H_{17}-$ | 1 | $C_8H_{17}$-(isomeric mixtures) |
| 26 | $CH_3\overset{O}{\underset{\|}{C}}-$ | $CH_3\overset{O}{\underset{\|}{C}}-$ | 1 | cyclohexyl-H, -C(CH_3)_3 |

APPLICATION EXAMPLE A

A clear finish of
80 Parts of Viacryl SC 344 (a 50% solution of an acryl resin from Vianova),
13.9 Parts of Maprenal MF 80 (a 72% solution of a melamine resin from Hoechst) and
4.1 Parts of Byketol OK (from Byk-Malinckrodt) is added to 2 parts of a compound of formula 1a (described in Example 1). After 1 minute the light stabiliser material so formed is dissolved in a finish. The finish is applied conventionally (according to the known 2 layer procedure) to a metallic or single pigment finish whilst still wet by spraying to form a layer having a thickness of 30 to 40 μm. The resulting coating is then hardened at 140° C. for 30 minutes. The coating shows very good resistance to U.V. light and weathering.

APPLICATION EXAMPLE B

A clear finish of
29.5 Parts of Setalux C-1502 XX-60 (a 60 % solution of an acryl resin from Synthese B.V.),
39.2 Parts of Setalux C-1382 BX-45 (a 45% solution of an acryl resin from Synthese B.V.),
21.4 Parts of Setamine US-138 BB-70 (a 70% solution of a melamine resin from Synthese B.V.),
2.5 Parts of Baysilonoil [(2% solution in Xylene) from Bayer] and
7.4 Parts of Depanol Y (a solvent from Hoechst)
is stirred together with 2.5 parts of a compound of formula 19a (described in Example 19) and 2 parts of an acid catalyst derived from phosphoric acid (Type: Catalyst 296-9 from American Cyanamid) to form a homogeneous mixture. The finish is applied conventionally (according to the known 2 layer procedure) to a metallic or single pigment finish whilst both are still wet by spraying to form a layer having a thickness of 30 to 40 μm. The resulting coating is then hardened at 110° C. for 20 minutes. The coating shows very good resistance to U.V. light and weathering.

APPLICATION EXAMPLE C

A clear finish of
75 Parts Macrynal SH 510N (a hydroxy containing acryl resin from Bayer)
2 Parts of Baysilon-oil A [(1% solution in xylene) from Bayer]
0.3 Parts of dibutyl zinc dilaurate
0.35 Parts diethanolamine
5.0 Parts of ethylglycol acetate
5.0 Parts of Solvesso 100
6.0 Parts of Xylene and
6.35 Parts of butyl acetate
is added to 23.5 parts of a compound of formula 2a (described in Example 2) and 30 parts of Desmodur N 75 (from Bayer). The homogeneous mixture so formed is applied conventionally (according to the known 2 layer procedure) to a metallic or single pigment finish whilst both are still wet by spraying to form a layer having a thickness of 30 to 40 μm and the resulting coating is hardened over 20 minutes at 80° to 90° C. The resulting 2K-PUR coating shows a good resistance to U.V. light and weathering.

APPLICATION EXAMPLE D

A single white pigmented finish of
14.30 Parts of Setamine US-132 BB 70 (a 70 % solution of a melamine resin from Synthese)
57.15 Parts of Setal 84 W-70 (a 70 % solution of an alkyd resin from Synthese)
7.70 Parts of n-butanol
1.85 Parts of butylglycol acetate
9.50 Parts of Xylene and
25 Parts of titanium dioxide (Rutil type)
is added with 1.38 parts of the product of Example 11 (see Table 1). The finish is conventioanlly applied to a grounded steel metal to which a filler of layer thickness 20 to 30 μm has been annealed, by spraying and after standing for 30 minutes at room temperature the steel metal surface is annealed at 120° C. for 30 minutes. The resulting coating shows very good resistance to U.V. light and weathering.

In Application Examples A to D instead of the product of the named example (e.g. Example 1, 19, 2 and 11 respectively) the product of any one of the other Examples 1 to 26 can be used.

What is claimed is:
1. A compound of the formula

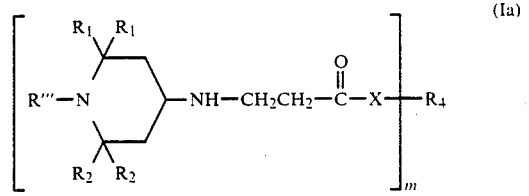

in which
R''', is hydrogen, methyl or $CH_3CO-$;
both $R_1$'s are $CH_3$ or together form $-(CH_2)_5$;
both $R_2$'s are $CH_3$ or together form $-(CH_2)_5$;
X is a $-O-$, $-NH-$ or

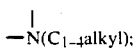

$-N(C_{1-4}alkyl)$;

m is an integer from 1 to 4, inclusive;
R₄, when m is 1, is $C_{8-18}$alkyl, $C_{1-8}$alkoxy $C_{1-12}$alkyl or $C_{1-6}$ hydroxyalkyl, when m is 2, is —CH₂)ₙ,

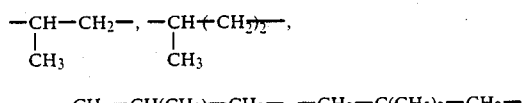

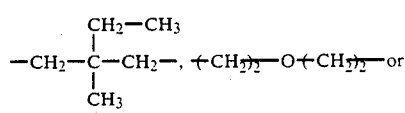

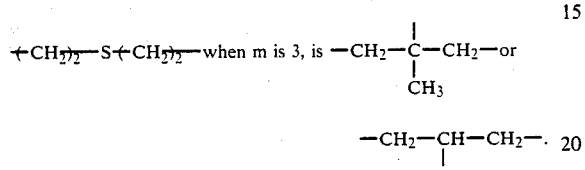

when m is 4, is C—(CH₂)₄; and n is 2 to 14.

2. A solid masterbatch composition containing 20 to 80% by weight of a compound according to claim 1 and 80 to 20% by weight of a solid thermoplastic polymer.

3. A liquid stoving automotive finish for application to a metal surface, containing 0.02 to 5% by weight of a compound according to claim 1.

4. A product of claim 3 which is a two layer finish in which the top coat is clear and the base coat contains a single pigment or metallic flakes.

5. A liquid automotive finish in which the binder material is between 35% and 70% by weight of said finish, to which a compound according to claim 1 is added as a solution in an organic solvent.

6. A concentrate composition in an organic solvent for use in a finish for stoving in which a compound according to claim 1 is present in at least 40% by weight of the total concentrate.

7. A compound of claim 1 in which X is O.
8. A compound of claim 1 in which R is hydrogen.
9. A compound of claim 1 in which each of R₁ and R₂ are CH₃.
10. A compound according to claim 1 of the formula

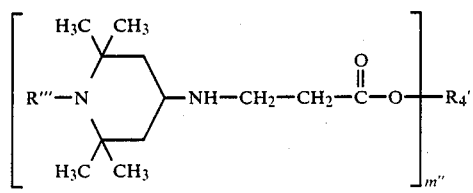

wherein
m" is 1 or 2;
R₄′, when m" is 1, is $C_{8-18}$alkyl, $C_{1-8}$alkoxy $C_{1-12}$alkyl or $C_{1-6}$hydroxy alkyl, and, when m" is 2, is —(CH₂)ₙ″— or —(CH₂)₂—O—(CH₂)₂— and
n" is 4, 6 or 8.

11. A compound according to claim 1 wherein m is 3 or 4.
12. A compound according to claim 10 wherein m" is 1, R‴ is hydrogen and R₄′ is ethylhexyl.
13. A compound according to claim 10 wherein m" is 2, R‴ is hydrogen and R₄′ is —(CH₂)₆—.

14. A compound of the formula

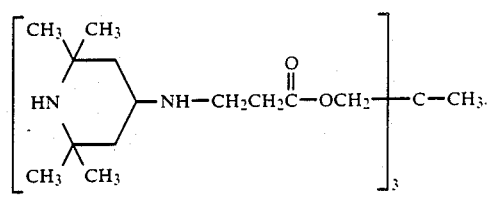

15. A process for stabilizing a polymeric material against the effect of light which comprises incorporating into the polymeric material form 0.01 to 5% by weight of a compound of the formula

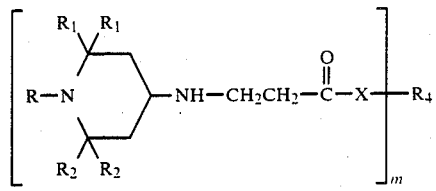

wherein
R is hydrogen, unsubstituted $C_{1-18}$alkyl, unsubstituted $C_{1-12}$alkyl carbonyl or oxygen;
both R₁'s are CH₃ or together form —(CH₂)₅;
both R₂'s are CH₃ or together form —(CH₂)₅;
X is —O—, —NH— or —N($C_{1-4}$alkyl)-;
m is an integer from 1 to 4, inclusive;
R₄,
when m is 1, is $C_{8-18}$alkyl, $C_{1-8}$alkoxy $C_{1-12}$alkyl or $C_{1-6}$ hydroxyalkyl,
when m is 2, is

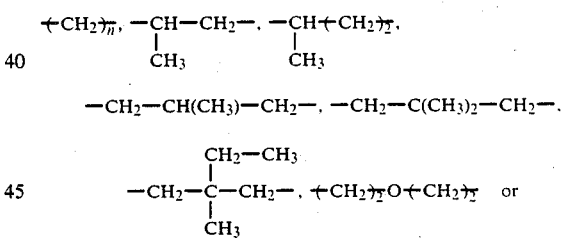

when m is 3, is

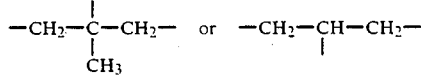

when m is 4, is C—(CH₂)₄; and
n is 2 to 14.

16. A process for stabilizing a polymeric material against the effect of light which comprises incorporating into the polymeric material from 0.01 to 5% by weight of a compound according to claim 1.

17. A polymeric material stabilized against the effects of light by the process of claim 15.

18. A polymeric material stabilized against the effects of light containing 0.01 to 5% by weight of a compound according to claim 10.

19. A cured automotive finish obtained by applying and stoving a two layer metallic liquid stoving auotmotive finish wherein the top coat contains a stabilizing amount of a compound according to claim 1.

20. A cured automotive finish according to claim 19 wherein the top coat is clear and the base coat contains a single pigment or metallic flakes.

21. A concentrate composition in an organic solvent for use in a finsih for stoving in which a compound according to claim 10 is present in an amount by weight of from 60 to 80% of the total concentrate.

22. A polymeric material stabilized against the effects of light containing 0.2 to 2%, by weight, of a compound according to claim 1.

23. A polymeric material stabilized against the effects of light containing 0.2 to 2%, by weight, of a compound according to claim 10.

24. A polymeric material stabilized against the effects of light by the process of claim 15 wherein the amount of compound of the formula defined in claim 27 is 0.2 to 2%, by weight.

25. A cured automotive finish obtained by applying the liquid stoving finish of claim 3 to a metal surface and stoving said finish.

* * * * *